(12) United States Patent
Harris (10) Patent No.: US 7,651,482 B2
(45) Date of Patent: Jan. 26, 2010

(54) NON-CORING NEEDLES AND METHODS OF MANUFACTURING SAME

(75) Inventor: Chad Harris, Albertville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/049,645

(22) Filed: Feb. 4, 2005

(65) Prior Publication Data

US 2006/0178646 A1    Aug. 10, 2006

(51) Int. Cl.
*A61M 5/00* (2006.01)

(52) U.S. Cl. .................................. 604/272

(58) Field of Classification Search ................ 604/264, 604/164.01, 268, 164.11, 164.08, 274, 272, 604/275, 273
See application file for complete search history.

(56) References Cited

U.S. PATENT DOCUMENTS

| | | | | |
|---|---|---|---|---|
| 1,084,845 | A * | 1/1914 | Stevens | 123/41.49 |
| 2,717,599 | A * | 9/1955 | Huber | 604/274 |
| 4,274,408 | A * | 6/1981 | Nimrod | 604/165.02 |
| 4,585,446 | A * | 4/1986 | Kempf | 604/274 |
| 4,826,492 | A | 5/1989 | Magasi | |
| 4,842,585 | A * | 6/1989 | Witt | 604/158 |
| 4,921,479 | A * | 5/1990 | Grayzel | 604/509 |
| 5,201,712 | A * | 4/1993 | Bryant | 604/164.02 |
| 5,261,891 | A * | 11/1993 | Brinkerhoff et al. | 604/164.12 |
| 5,312,345 | A * | 5/1994 | Cole | 604/110 |
| 6,106,499 | A * | 8/2000 | Overton et al. | 604/170.01 |
| 6,478,775 | B1 * | 11/2002 | Galt et al. | 604/158 |
| 6,491,670 | B1 * | 12/2002 | Toth et al. | 604/264 |
| 6,638,251 | B2 * | 10/2003 | Steube et al. | 604/158 |
| 6,676,636 | B2 * | 1/2004 | Chang et al. | 604/164.02 |
| 2003/0153879 | A1 * | 8/2003 | Luther | 604/272 |
| 2004/0193121 | A1 | 9/2004 | Kadziauskas et al. | |
| 2005/0215977 | A1 * | 9/2005 | Uschold | 604/506 |

FOREIGN PATENT DOCUMENTS

| | | |
|---|---|---|
| DE | 44 46 677 A1 | 7/1996 |
| EP | 0 271 775 A2 | 6/1988 |
| FR | 2 757 405 A1 | 6/1998 |
| FR | 2 845 276 A1 | 9/2002 |
| WO | WO 90/01349 | 2/1990 |

\* cited by examiner

*Primary Examiner*—Nicholas D Lucchesi
*Assistant Examiner*—Christopher D Koharski
(74) *Attorney, Agent, or Firm*—Kenyon & Kenyon LLP (57) ABSTRACT

The present invention discloses needles configured to prevent or reduce contact of tissue or other material with the heel of the needle to prevent coring of the tissue or other material by the heel of the needle. Also provided are needles having no heels or blunted heels. The present invention also provides methods of manufacturing needles having obstructed or blunted heels.

8 Claims, 15 Drawing Sheets

NON-CORING NEEDLES AND METHODS OF MANUFACTURING SAME

FIELD OF THE INVENTION

The present invention relates to needles that minimize or prevent damage to the site in which the needles are inserted.

BACKGROUND OF THE INVENTION

Needles have a wide variety of applications in the medical field. For instance, needles are used to delivery therapeutic agents, collect bodily fluids, and fill drug delivery ports. In many such applications, there is a desire to avoid or reduce damage to the site in which the needle is inserted. For example, drug delivery ports such as intravascular drug access devices often include a chamber for holding a therapeutic agent and a pierceable rubber septum for receipt of a needle to either fill or empty the chamber. Repeated piercing of the septum with the needle can damage the septum leading to infusion of the septum fragments into the patient's vascular system or into any catheter or other device having access to the port, thereby occluding the port.

With respect to delivering a therapeutic agent to a target site in the body, particularly directly delivering a therapeutic agent to a target site, current injection needles have beveled open ends with Lancet point tips. Such open-ended needles have the potential to core tissue as the needles penetrate the tissue. In the case of directly delivering a therapeutic agent to a myocardial wall of the heart, since most myocardial direct injection procedures involve injecting a therapeutic agent into the left ventricle walls, the risk of tissue embolism into the left ventricular cavity exists.

Needle tips, such as the "pencil-point" needle and the "Huber" needle have been developed that attempt to reduce coring by the needle. A Huber needle has a distal portion with a lateral bend and a laterally facing opening. The needle terminates in a sharpened closed tip. A pencil-point needle has a lateral opening and a closed tip at the distal end. Because there are no distal openings in these types of needles, any therapeutic agent that passes through the lumens of these needles exits these laterally facing openings, which will direct the therapeutic agent in a radial direction. Such radial delivery may result in the therapeutic agent being ejected or squeezed back through its point of entry in the target site. This problem is exacerbated in situations where the therapeutic agent is injected into an actively contracting tissue such as the myocardium of the heart. In such a case, the therapeutic agent may be ejected or squeezed out through its point of entry by the repeated expansion and contraction of the heart muscle. This unintended and unwanted leakage can result in an unascertainable dosage of the therapeutic being ultimately received by the target site and arbitrary and unwanted interaction between leaked therapeutic agent and neighboring tissue and muscle.

Accordingly, there is a need for a needle that will prevent or minimize damage to the site in which the needle is inserted and that will direct the delivery of a therapeutic agent, or any infusion material, in a distal direction out of the needle.

SUMMARY OF THE INVENTION

In certain embodiments, the present invention provides a needle comprising a shaft having a heel and an infusion lumen extending therethrough and a buffer disposed within the infusion lumen of the shaft. The buffer has a blunt distal end obstructing the heel of the shaft.

In certain embodiments, the present invention provides a needle for delivering an infusion material to a target site that comprises a shaft having a longitudinal axis, an infusion lumen extending therethrough, and a distal end terminating in a closed tip. The distal end of the shaft defines at least one lateral port that is offset from the longitudinal axis of the shaft. The at least one lateral port is angled in a direction to direct flow of the infusion material in a distal direction.

In certain embodiments, the present invention provides a needle comprising a shaft having a distal surface, an inlet port and an outlet port, and an infusion lumen extending between the inlet port and the outlet port. The needle further comprises an elongated penetration member slidably disposed within the infusion lumen of the shaft. The penetration member comprises a stem and a head portion, which has a closed distal tip and a proximal surface. The penetration member is capable of having a retracted configuration and an extended configuration. In a retracted configuration, the proximal surface of the head portion abuts against the distal surface of the shaft to close the outlet port and in an extended configuration, the head portion distally extends away from the distal surface of the shaft to open the outlet port.

In certain embodiments, the present invention provides a needle comprising a cannulated shaft having a longitudinal axis and a distal end. The distal end has a trailing portion and a leading portion terminating in a pointed tip. The leading portion, according to these embodiments of the present invention, is angled towards the trailing portion.

In certain embodiments, the present invention provides a needle comprising a shaft having a distal end and opposing first and second inner walls that mutually define an infusion lumen. The distal end, according to these embodiments of the present invention, has a blunted heel.

BRIEF DESCRIPTION OF THE DRAWINGS

The present invention will become more fully understood from the detailed description given hereinbelow and the accompanying drawings which are given by way of illustration only and wherein.

DETAILED DESCRIPTION OF THE INVENTION

Figure 1:
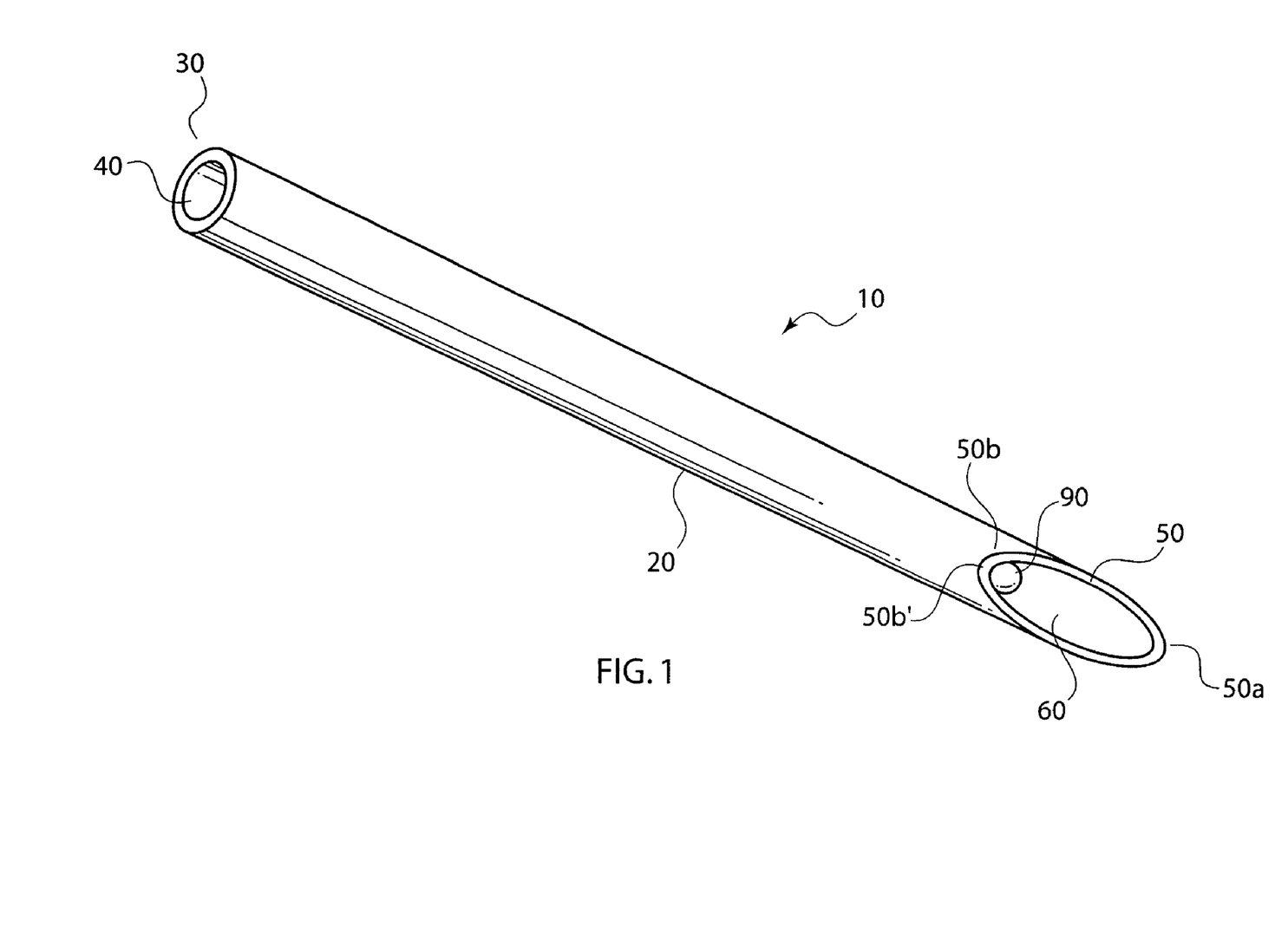
FIG. 1 is a perspective view of an embodiment of a needle according to an aspect of the present invention.
Figure 2:
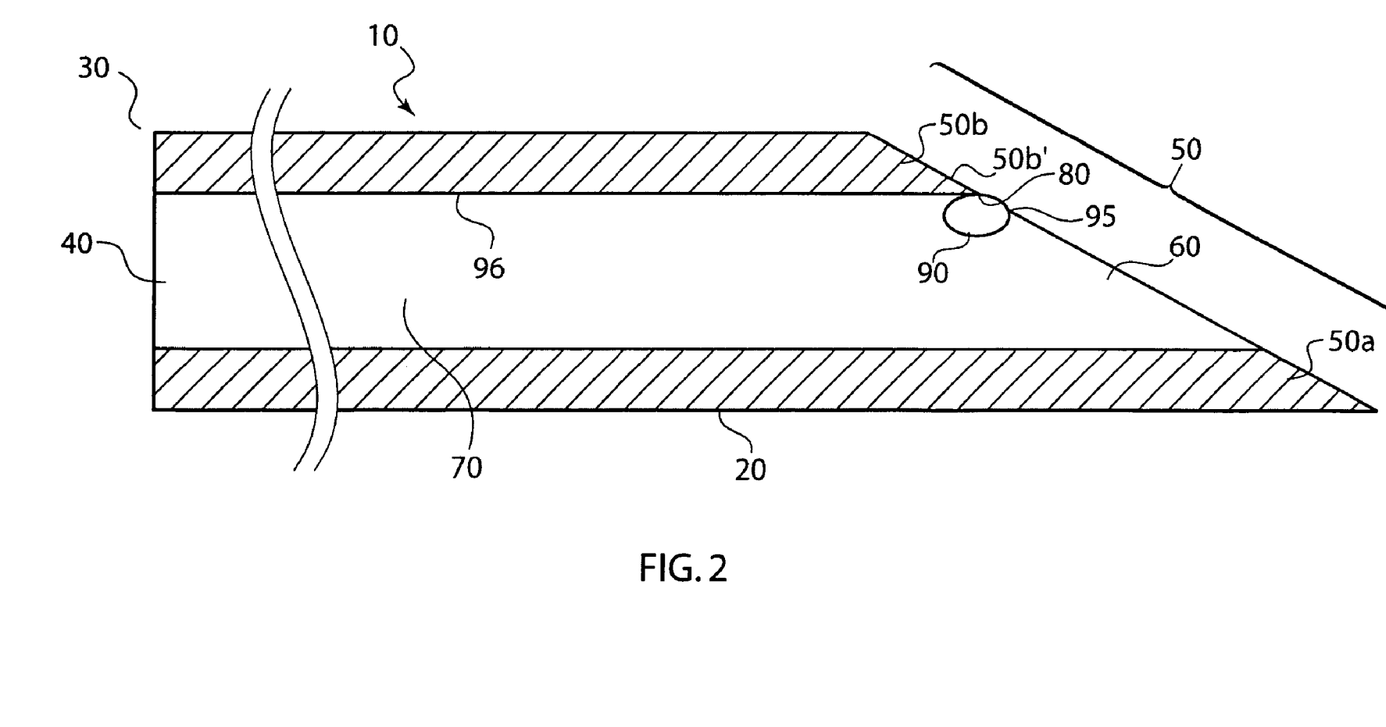
FIG. 2 is a cross-sectional view of an embodiment of a needle according to an aspect of the present invention.

Referring to FIG. 1, one embodiment of the present invention provides a needle 10 for delivering an infusion material to a target site that comprises a shaft 20 having a proximal end 30 defining an inlet port 40 and a distal end 50 (referred to herein as the bevel of shaft 20) defining an outlet port 60. Bevel 50 has a leading portion 50a and a trailing portion 50b that includes a trailing surface 50b'. Referring to FIG. 2, which is a cross-sectional view of needle 10 of FIG. 1, shaft 20 also has an annular inner wall 96 that defines an infusion lumen 70 extending between inlet port 40 and outlet port 60. Bevel 50 of shaft 20 has a heel 80, which is the edge of bevel 50 where trailing surface 50b' and inner wall 96 meet. According to the present invention, a buffer 90 with a blunt distal end 95 obstructing heel 80 is disposed within infusion lumen 70 of shaft 20. Because blunt distal end 95 obstructs heel 80, it reduces or prevents contact of a target site with heel 80 since as needle 10 penetrates into the target site, the target site is exposed to blunt distal end 95 of buffer 90 instead of heel 80. Although blunt distal end 95 obstructs heel 80, it does not completely occlude outlet port 60 thereby allowing any infusion material that passes through needle 10 to be directed out of outlet port 60 in the distal direction.

Figure 3:
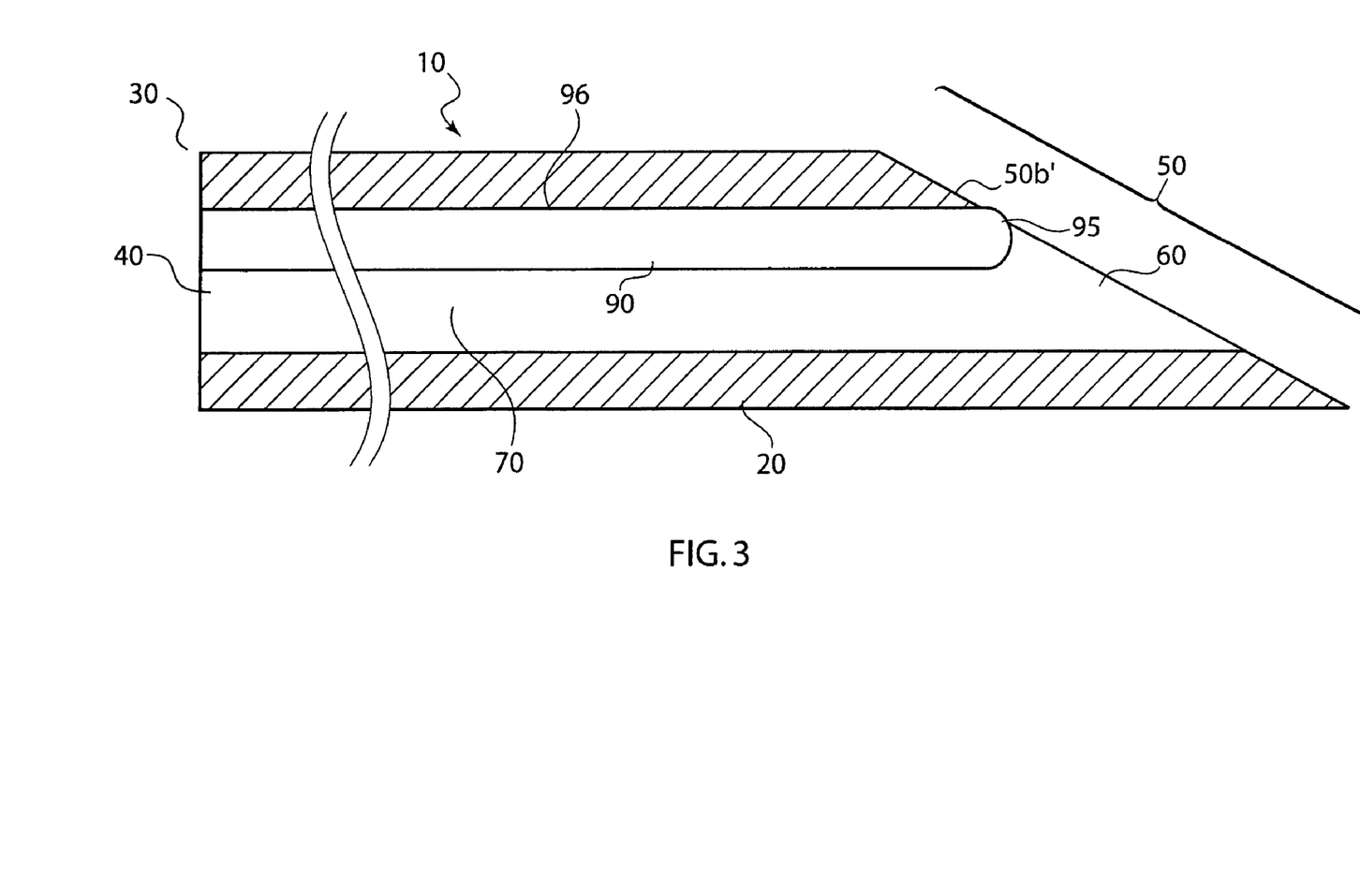
FIG. 3 is a cross-sectional view of an alternative embodiment of a needle according to an aspect of the present invention.
Figure 4:
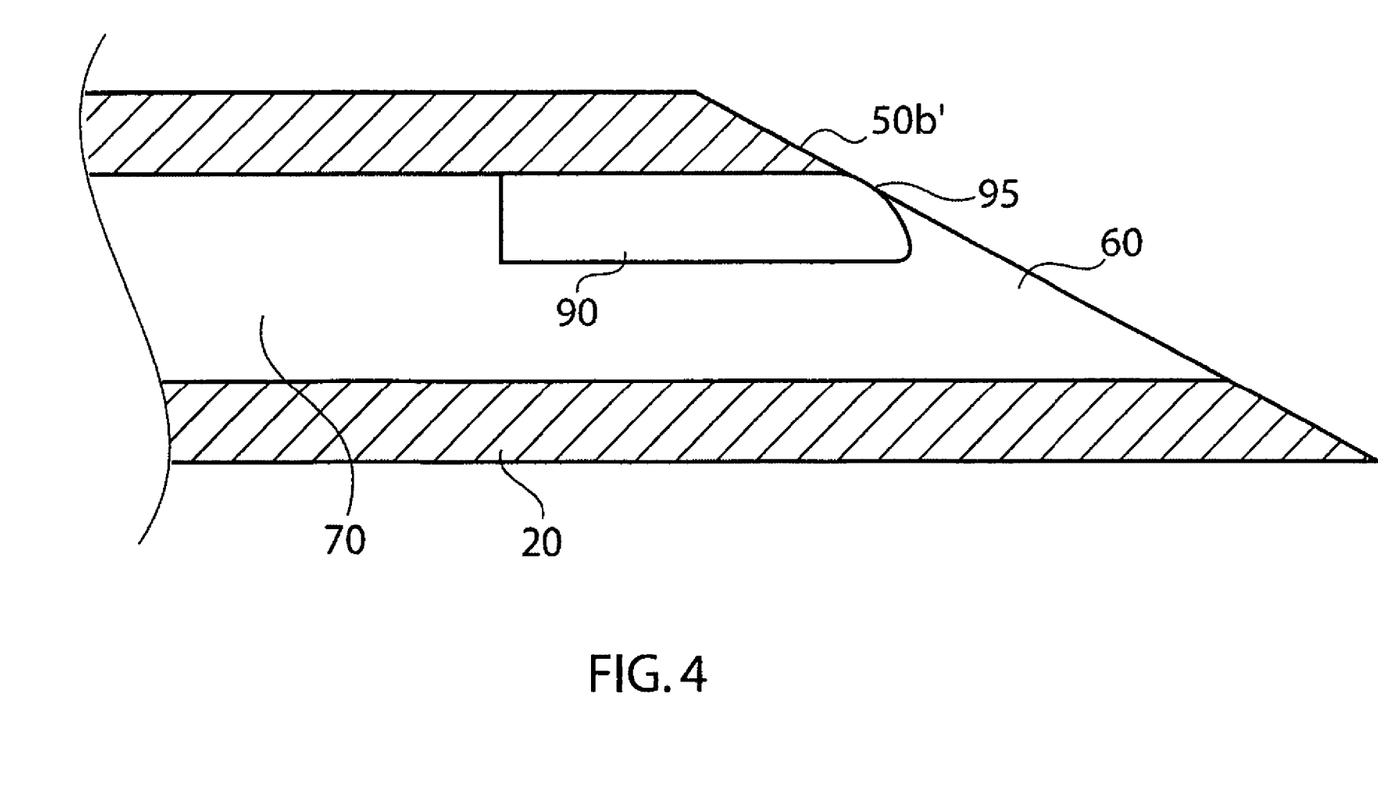
FIG. 4 is a cross-sectional view of an alternative embodiment of a needle according to an aspect of the present invention.
Figure 5:
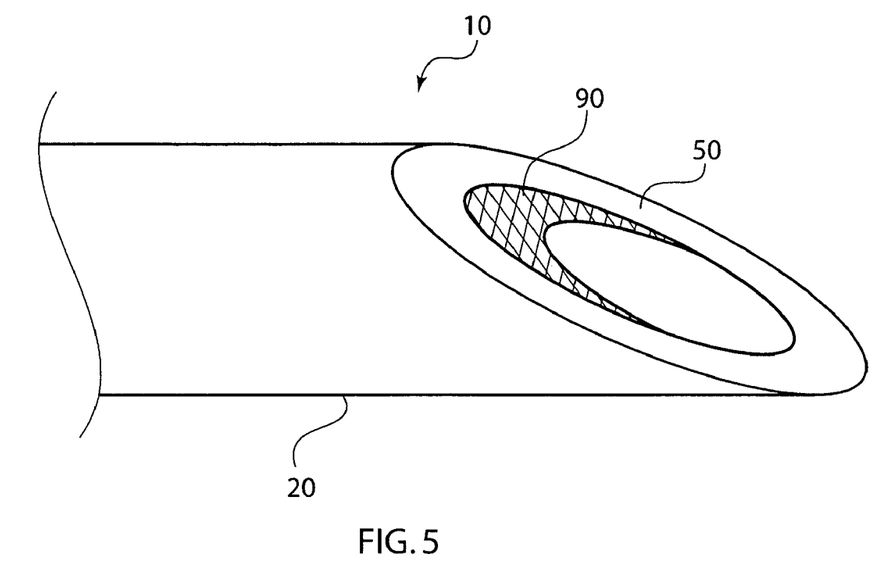
FIG. 5 is a perspective view of an alternative embodiment of a needle according to an aspect of the present invention.
Figure 6:
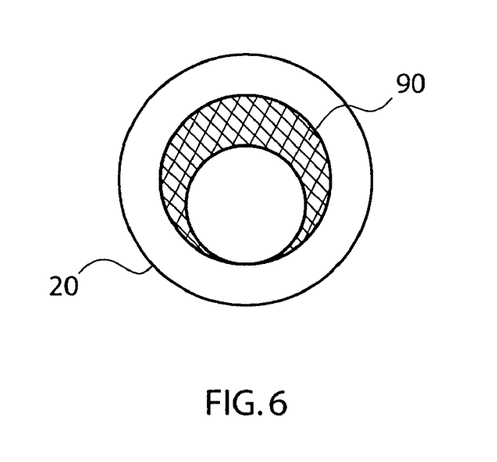
FIG. 6 is an end view of the needle depicted in FIG. 5.
Figure 7:
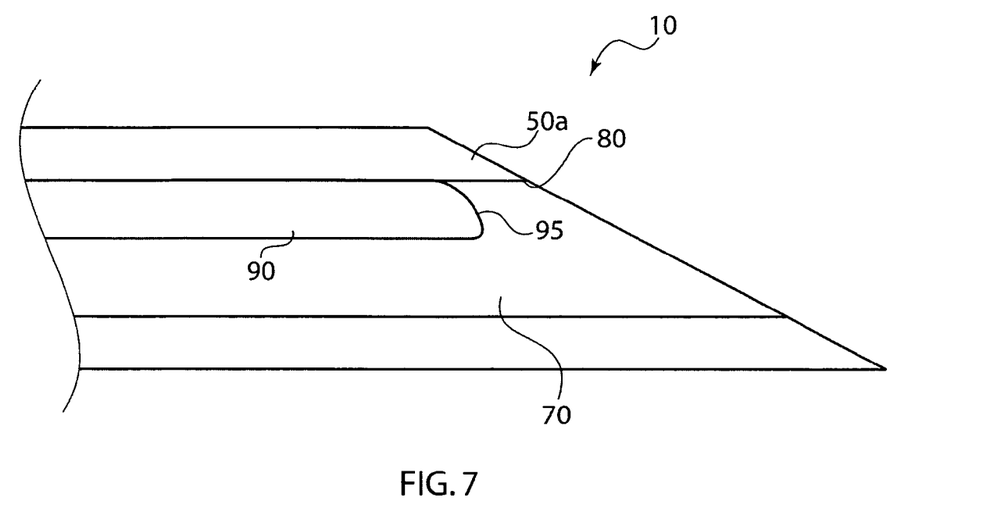
FIG. 7 is a cross-sectional view of an alternative embodiment of a needle with a buffer in a retracted configuration according to an aspect of the present invention.
Figure 8:
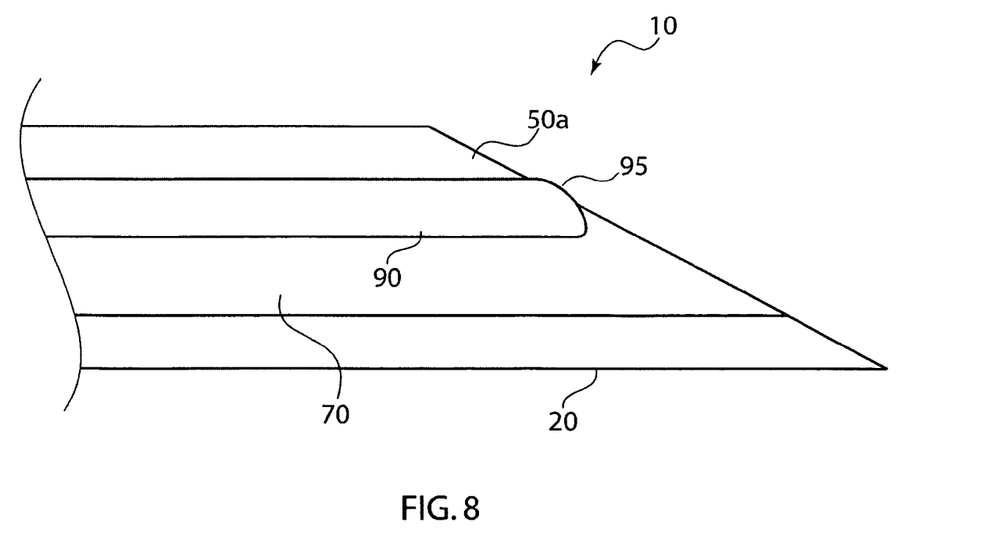
FIG. 8 is similar to FIG. 7 but depicting the buffer in an extended configuration.

Blunt distal end 95 of buffer 90 may have any configuration to effectively prevent or reduce coring of the target site by heel 80. For example, blunt distal end 95 may be completely rounded as illustrated in FIG. 3 or only partially rounded as illustrated in FIGS. 4, 7 and 8. Although preferably blunt distal end 95 extends slightly beyond infusion lumen 70 as illustrated in FIGS. 2 and 3, blunt distal end 95 may be located completely within infusion lumen 70 aligned with surface 50b' of trailing portion 50b as illustrated in FIG. 4. Furthermore, buffer 90, in its entirety, may have any configuration so long as distal end 95 remains blunt to effectively prevent or reduce coring of the target site by heel 80. For example, referring to FIG. 3, in one embodiment, buffer 90 has an elongated configuration such that buffer 90 spans the entire length of infusion lumen 70 between inlet port 40 and outlet port 60. Referring to FIG. 2, in another embodiment, buffer 90 has a spherical, pellet-like configuration such that buffer 90 only covers heel 80. Of course, buffer 90 may also have any intermediate size therebetween. For example, referring to FIG. 4, in another embodiment, buffer 90 does not span the entire length of infusion lumen 70 but contacts more than just heel 80 of bevel 50. Referring to FIG. 5, in another embodiment, buffer 90 is a webbing or plug that can be inserted into infusion lumen 70 and that has a crescent-shaped cross-sectional configuration (depicted in FIG. 6) such that buffer 90 covers heel 80 and the adjacent area of bevel 50.

Buffer 90 can be fixedly attached to or in slidable engagement with inner wall 96 of shaft 20. With respect to the latter embodiment, referring to FIGS. 7 and 8, buffer 90 may be slidably disposed in infusion lumen 70 to provide axial movement of buffer 90 within infusion lumen 70. For example, referring to FIG. 7, to initially penetrate the surface of the target site, buffer 90 can be retracted within infusion lumen 70 so that heel 80 is unobstructed during the initial entry process. Referring to FIG. 8, once the surface of the target site has been broken, buffer 90 can be axially extended to abut heel 80 so that heel 80 is covered during the remainder of the penetration process.

Buffer 90 may be fabricated of any biocompatible material such as a polymeric, woven, or metallic material (including stainless steel, nitinol, or other shape-memory materials). In order to further protect tissue, buffer 90 may be fabricated of an elastomeric material that provides a cushioning effect to the target site that contacts buffer 90. Buffer 90 may be separately molded into infusion lumen 70 against heel 80 or may be extruded into shaft 20 or co-extruded with shaft 20 during the fabrication of needle 10.

Figure 9:
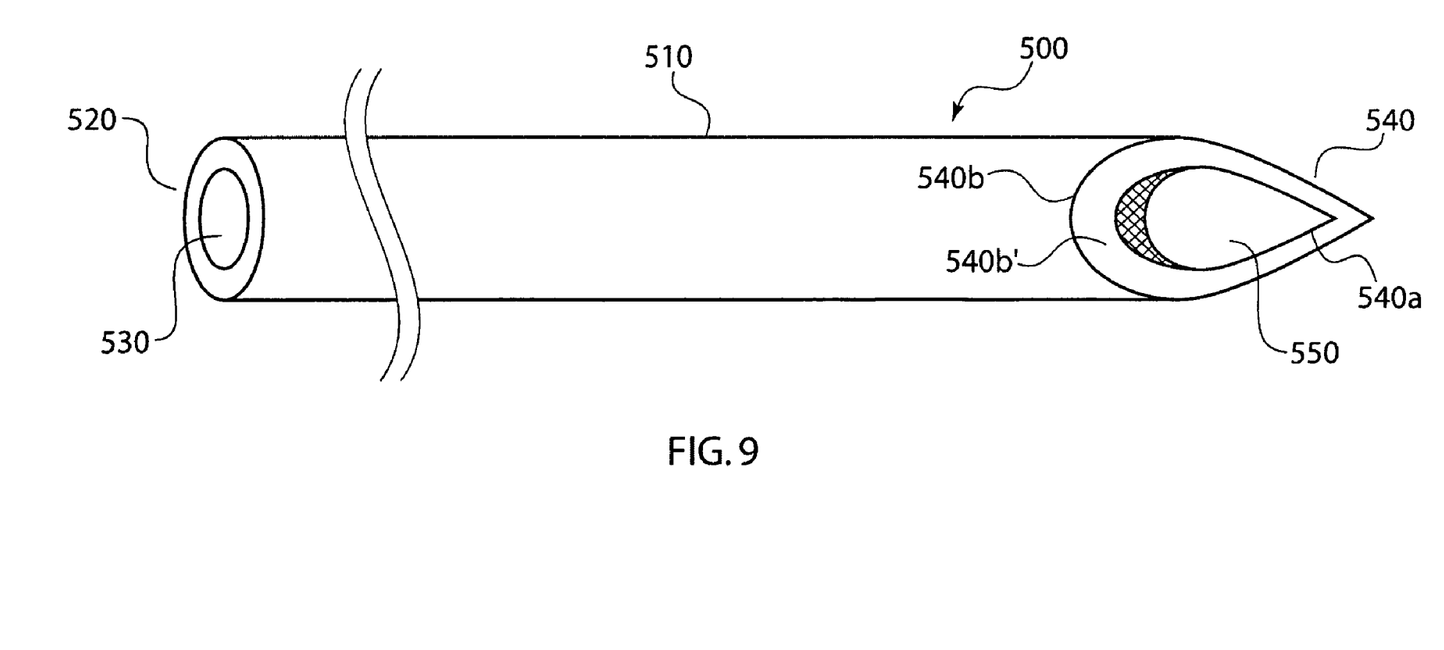
FIG. 9 is a perspective view of an embodiment of a needle according to another aspect of the present invention.

Referring to FIG. 9, another embodiment of the present invention provides a needle 500 comprising a shaft 510 having a proximal end 520 defining an inlet port 530 and a bevel 540 defining an outlet port 550. Bevel 540 has a leading portion 540a and a trailing portion 540b that includes a trailing surface 540b'. Referring to FIG. 10C, which is a cross-sectional view of needle 500 of FIG. 9, shaft 510 also has an annular inner wall 515 defining an infusion lumen 517 extending between inlet port 530 and outlet port 550. According to this embodiment of the present invention, bevel 540 of shaft 510 has a blunted heel 560 to reduce or eliminate any coring of a target site.

Figure 10A:
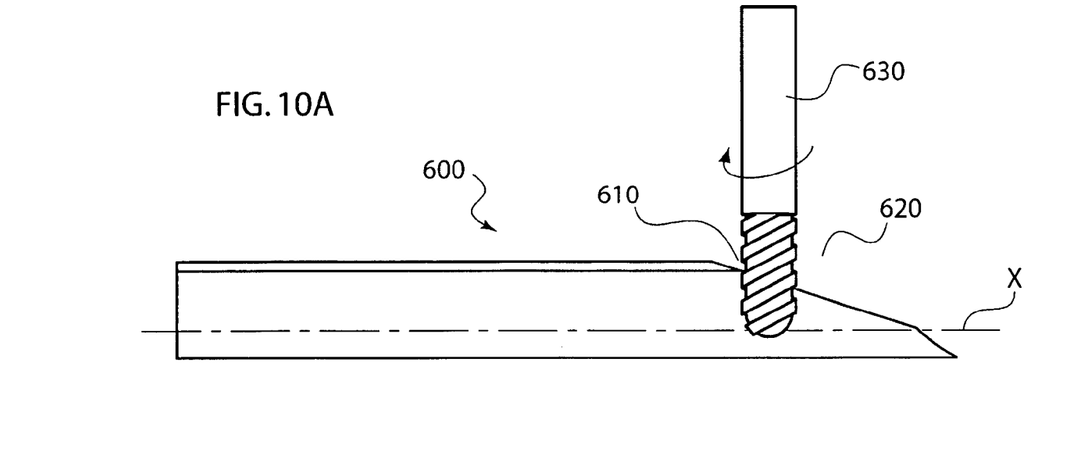
FIG. 10A depicts a stage of an embodiment of manufacturing the needle of FIG. 9.
Figure 10B:
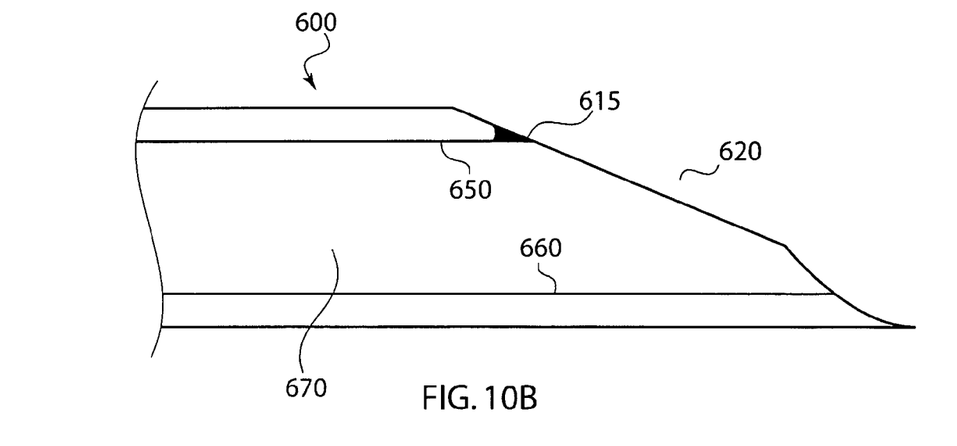
FIG. 10B depicts a stage of manufacturing the needle of FIG. 9.
Figures 10C, 10D:
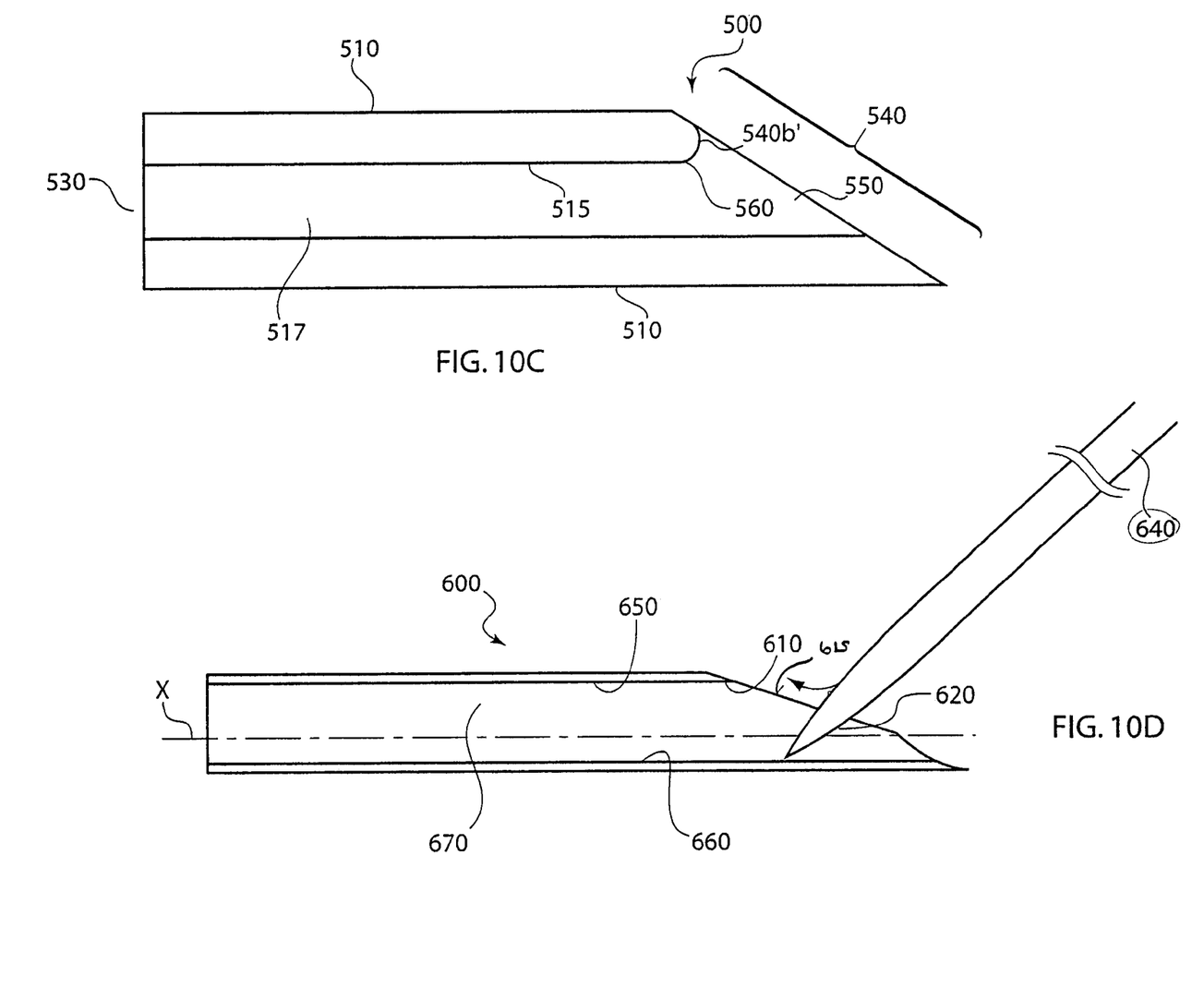
FIG. 10C depicts a stage of manufacturing the needle of FIG. 9.
FIG. 10D depicts a stage of an embodiment of an alternative embodiment of manufacturing the needle of FIG. 9.

Referring to FIGS. 10A-10D, in one embodiment, blunted heel 560 is formed by providing a pre-form needle 600 having a heel 610 at distal end 620 (illustrated in FIG. 10A) and machining distal end 620 to remove a portion 615 of heel 610 (illustrated in FIG. 10B) to form needle 500 of the present invention having a blunted heel 560 (illustrated in FIG. 10C). Distal end 620 of pre-form needle 600 may be machined by any means known in the art to remove portion 615 of distal end 620, such as by turning, drilling, milling, grinding, electrical discharge machining, electrochemical machining, abrasive flow machining, ultrasonic machining or other electrical, chemical or physical machining processes known to one of skill in the art. Referring to FIG. 10A, in one exemplary machining process, mill 630 is placed against distal end 620 in a position substantially perpendicular to longitudinal axis X of pre-form needle 600. Mill 630 is then rotated while moderate force is applied to heel 610 to mill away portion 615 of heel 560 to form needle 500 having blunted heel 560. Mill 630 may be rotated manually or such rotation may be automated through the use of a vise or other clamping device that receives mill 630.

Referring to FIG. 10D, in another embodiment, blunted heel 560 is formed by providing a pre-form needle 600 having a heel 610 at distal end 620 and having an annular inner wall defining an infusion lumen. Specifically, annular inner wall has a first side 650 and an opposing second side 660 that mutually define an infusion lumen 670. According to this method, a pick 640 is placed against distal end 620 at an angle to longitudinal axis X of pre-form needle 600. Pick 640 is rolled against distal end 620 while moderate pressure is applied to heel 610 to fold portion 615 of distal end 620 inwards into infusion lumen 670 towards first side 650 to form needle 500 of the present invention having blunted heel 560. As will be appreciated by one skilled in the art, other instruments may be used to fold portion 615 inwards into infusion lumen 670 of pre-form needle 600 to form needle 500 having blunted heel 560.

Figure 11:
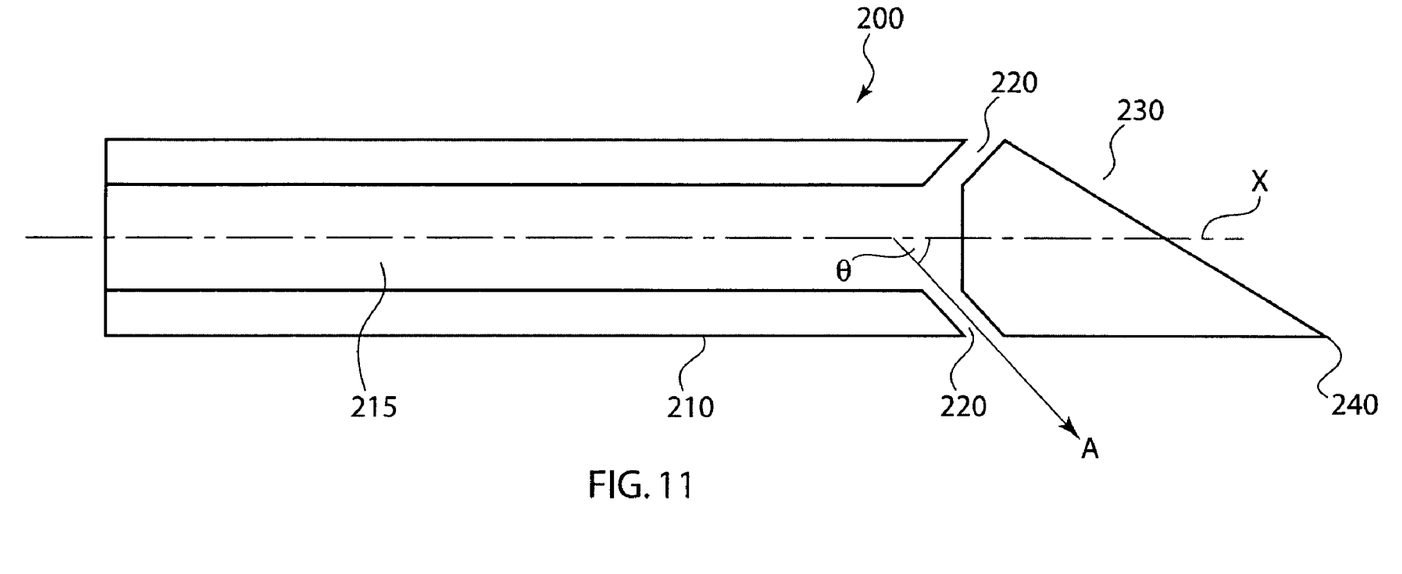
FIG. 11 is a cross-sectional view of a needle according to an embodiment of another aspect of the present invention.
Figure 12:
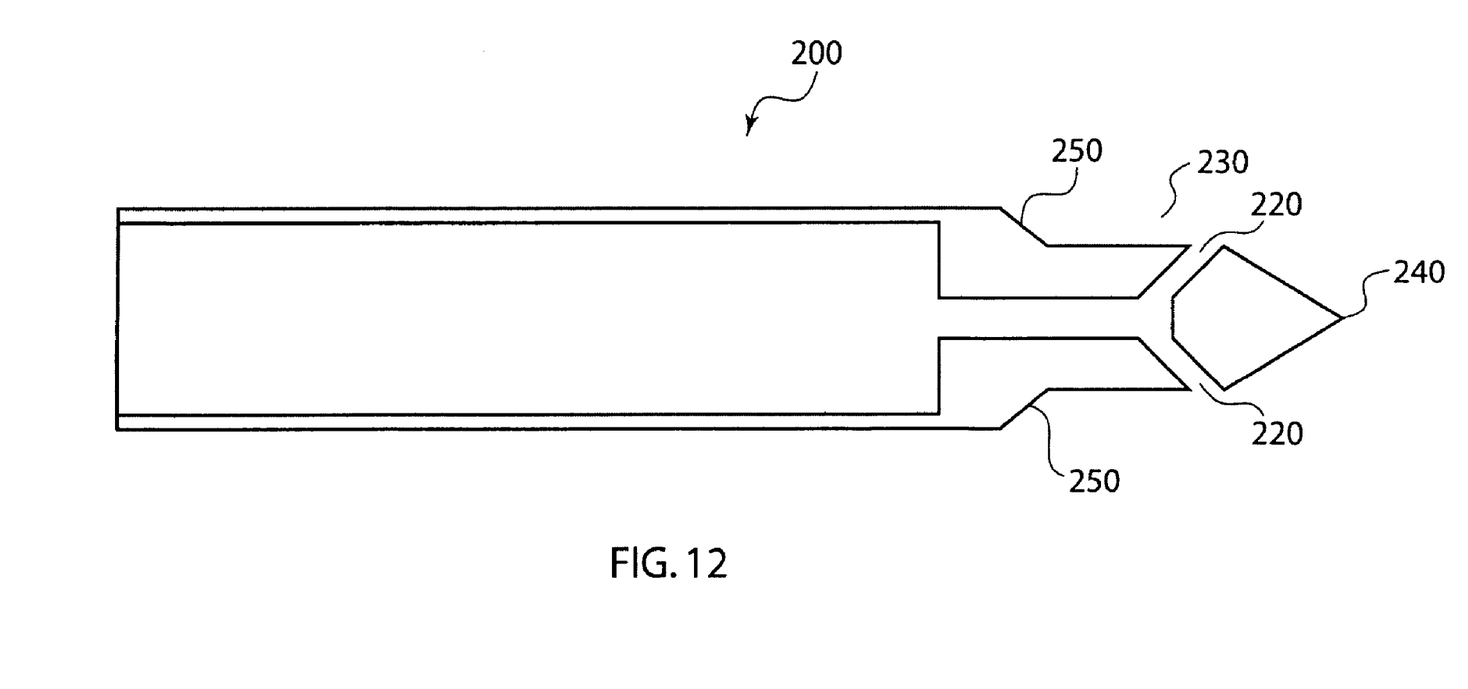
FIG. 12 is a cross-sectional view of a needle according to an alternative embodiment of another aspect of the present invention.

Referring to FIG. 11, another embodiment of the present invention provides a needle 200 for delivering an infusion material to a target site that comprises a shaft 210 having a longitudinal axis X, an infusion lumen 215 extending therethrough, and a distal end 230 terminating in a closed tip 240. According to this embodiment of the present invention, distal end 230 defines at least one lateral port 220 that is offset from longitudinal axis X of shaft 210 and that is angled in a direction to direct flow of infusion material in a distal direction. Because distal end 230 terminates in a closed tip 240, there is no opening through which tissue or any other material can enter, thereby eliminating any potential coring of the target site. However, needle 200 still provides for distal delivery of the infusion material, since lateral port 220 is angled to direct flow of the infusion material in a distal direction. Lateral port 220 is angled with respect to longitudinal axis X of shaft 210, and preferably the angle is selected such that the direction of flow A through lateral port 220 is angled at an angle θ less than 90 degrees with respect to longitudinal axis X. Also preferably, the at least one lateral port 220 comprises a plurality of lateral ports 220 to provide more flow and create less infusion pressure through needle 200. More preferably, each of the plurality of lateral ports 220 are staggered such that each port 220 is located on a different plane of shaft 210 to provide distal end 230 with more column strength. Referring to FIG. 12, in a preferred embodiment, distal end 230 is swaged such that distal end defines a pair of ridges 250, which block any backward leakage of infusion material from the target site once the infusion material has been delivered to the target site.

Figure 13:
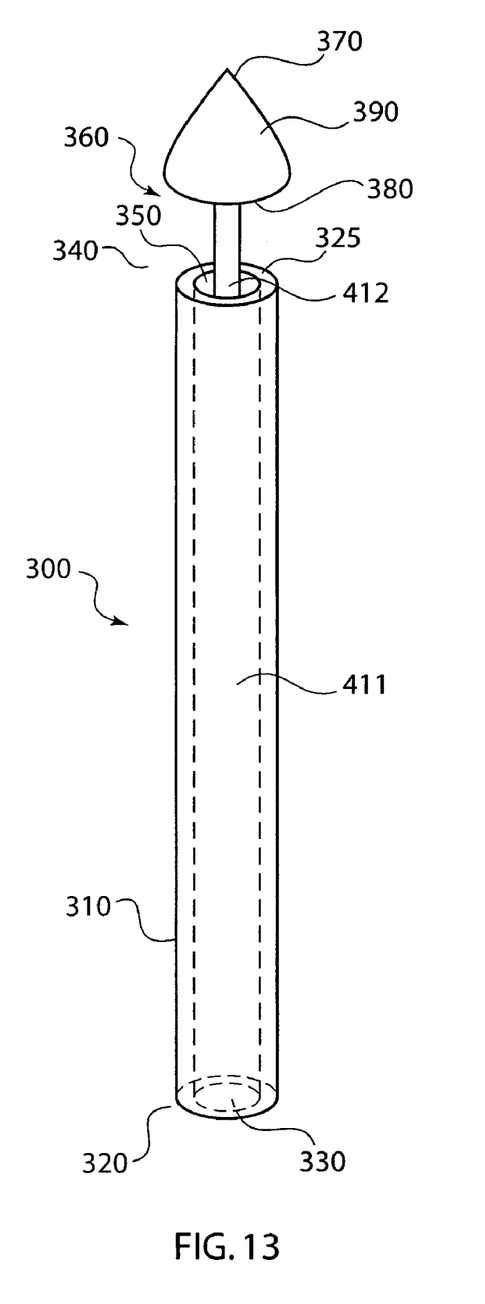
FIG. 13 is a perspective view of a needle comprising a penetration member in an extended configuration according to an aspect of the present invention.
Figure 14:
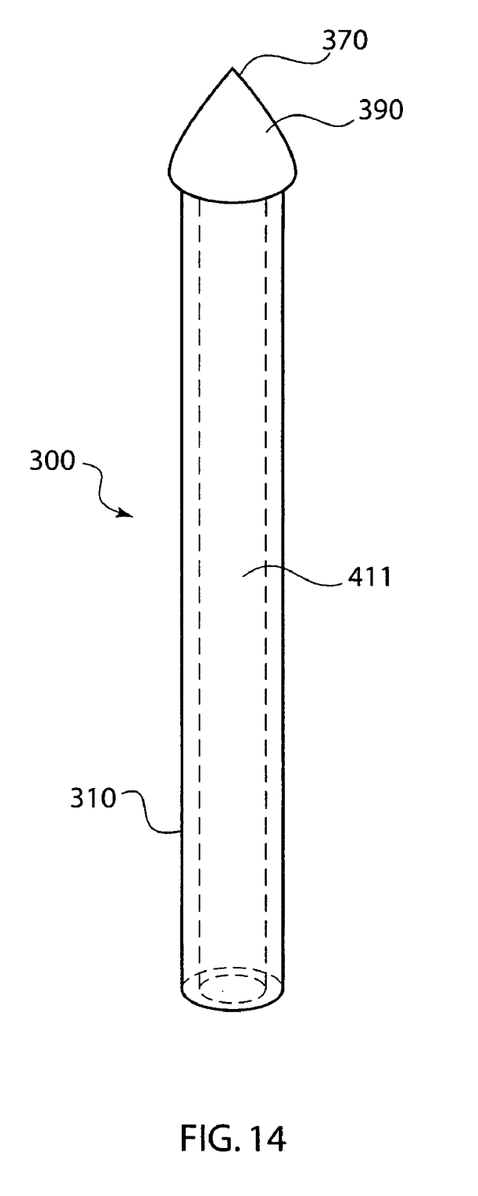
FIG. 14 is similar to FIG. 13 but depicting the penetration member in a retracted configuration.
Figure 15:
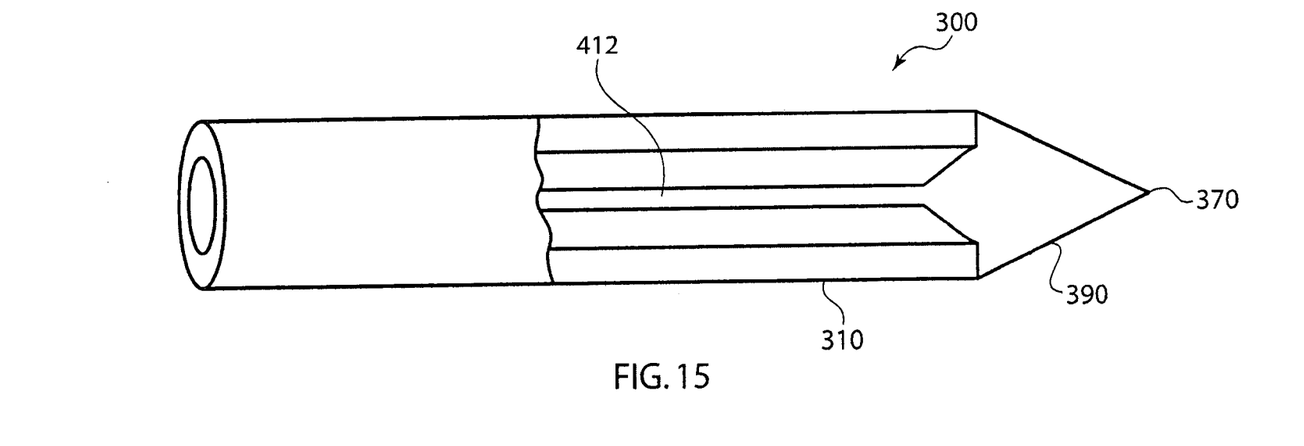
FIG. 15 is a cross-sectional view of a needle comprising an alternative embodiment of a penetration member in a retracted configuration according to an aspect of the present invention.
Figure 16:
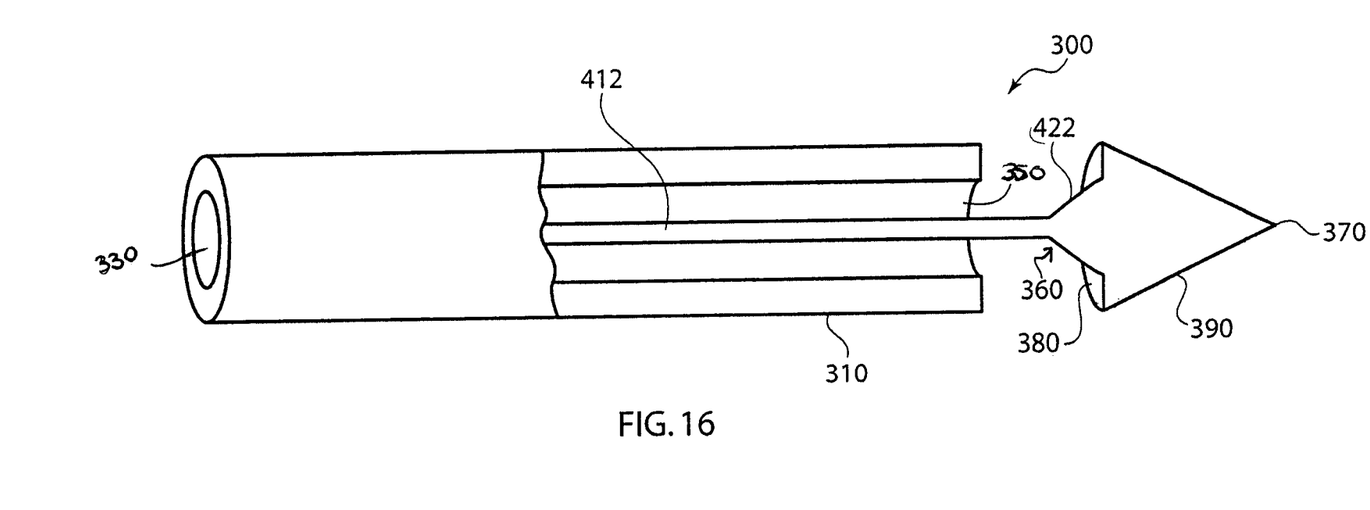
FIG. 16 is similar to FIG. 15 but depicting the penetration member in an extended configuration.

Referring to FIGS. 13 and 14, another embodiment of the present invention provides a needle 300 comprising a shaft 310 having a proximal end 320 defining an inlet port 330, a distal end 340 defining an outlet port 350, and an infusion lumen 411 extending between inlet port 330 and outlet port 350. Specifically, distal end 340 has an annular distal surface 325 that defines outlet port 350. According to this embodiment of the present invention, needle 300 further comprises a penetration member 360 having an elongated stem 412 and a terminal head 390. Head 390 has a proximal surface 380 and a pointed closed distal tip 370. Penetration member 360 is capable of having an extended configuration, as illustrated in FIG. 13 and a retracted configuration, as illustrated in FIG. 14. Referring to FIG. 14, in a retracted configuration, proximal surface 380 of head 390 abuts against distal surface 325 of shaft 310 to close outlet port 350. Referring to FIG. 13, in an extended configuration, head 390 distally extends away from distal surface 325 to open outlet port 350. Referring to FIGS. 15 and 16, proximal surface 380 of head 390 may define a swaged end 422 that is received by outlet port 350 in a retracted configuration of penetration member 360. In use, needle 300 penetrates into the target site while penetration member 360 is in a retracted configuration. Because outlet port 350 is closed in a retracted configuration of penetration member 360 (and distal tip 370 is closed), needle 300 does not core or damage the target site into which needle 300 is inserted. After penetration by needle 300 is complete, needle 300 remains stationary and penetration member 360 assumes an extended configuration to open outlet port 350. Once outlet port 350 is open, infusion material can pass through infusion lumen 411 to the target site.

Figure 17:
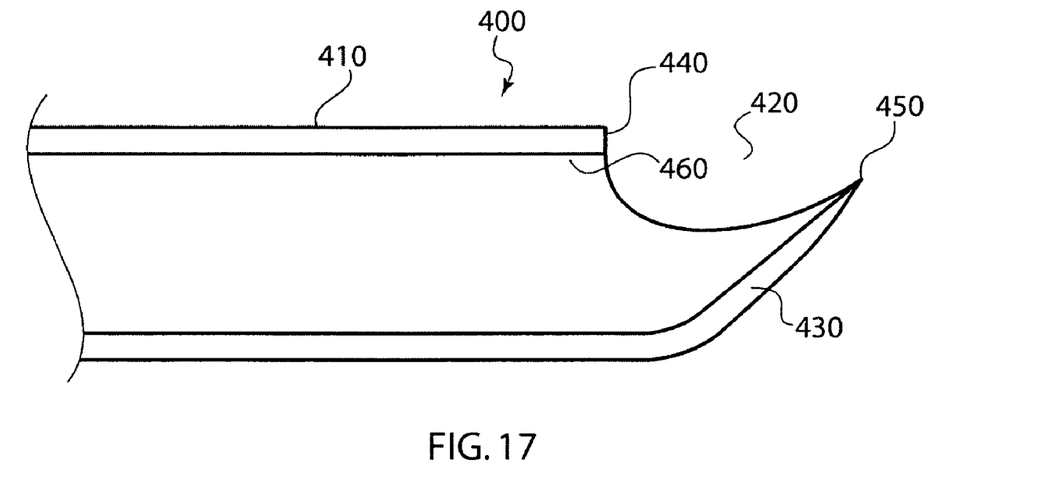
FIG. 17 is a side view of an embodiment of a needle according to another aspect of the present invention.
Figure 18:
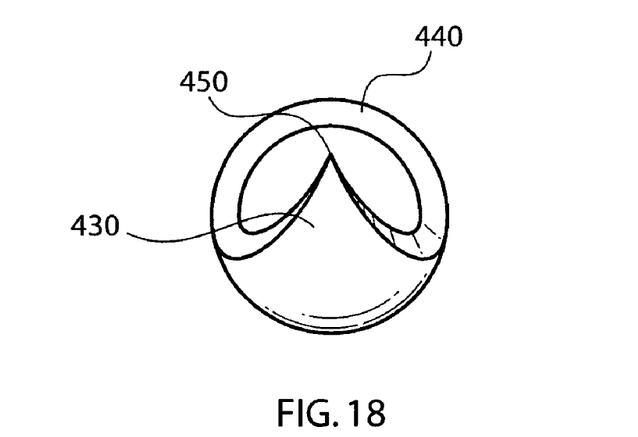
FIG. 18 is an end view of the needle depicted in FIG. 17.
Figure 19A:
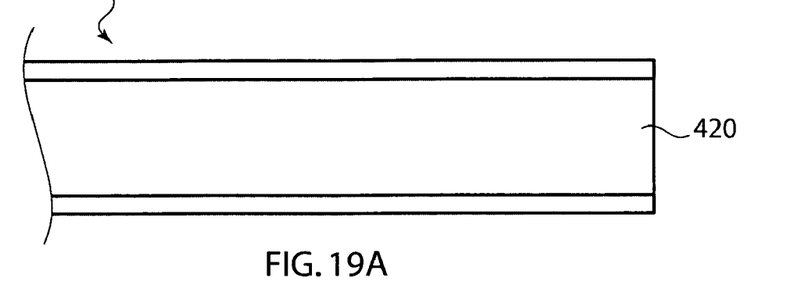
FIGS. 19A-19D depict respective stages of manufacture of the needle depicted in FIG. 17.
Figure 19B:
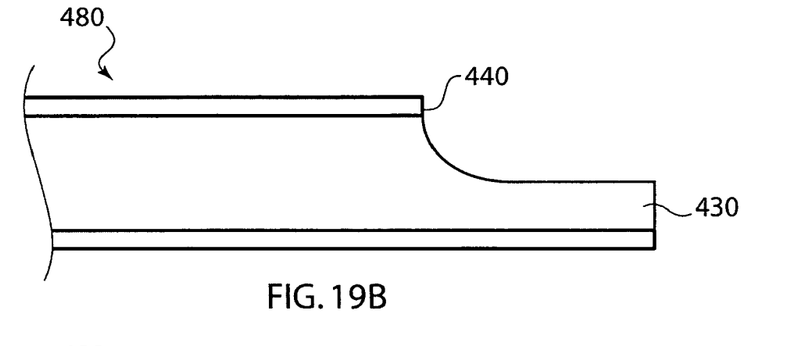
Figure 19C:
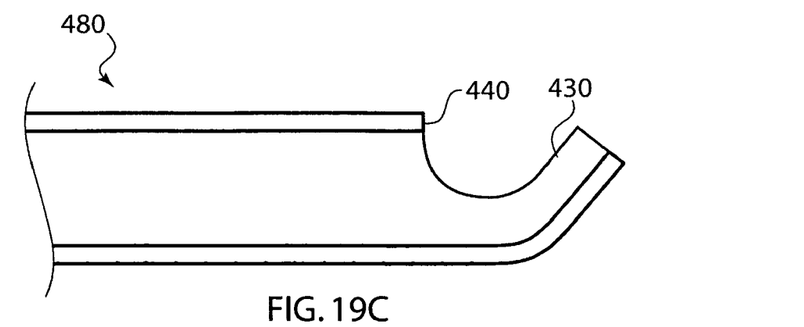
Figure 19D:
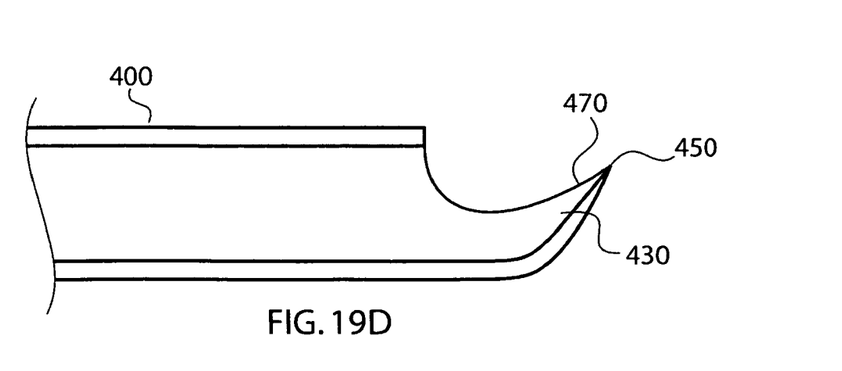

Referring to FIGS. 17 and 18, in another embodiment, the present invention provides a needle 400 comprising a cannulated shaft 410 having a distal end 420. Distal end 420 has a trailing portion 440 and a leading portion 430 that terminates in a pointed tip 450. According to this embodiment of the present invention, leading portion 430 is angled towards trailing portion 440. Such a configuration of needle 400 eliminates contact between the target site and heel 460 since leading portion 430 essentially masks or blocks heel 460 as needle 400 is inserted into the target site, thereby preventing any coring of the target site by heel 460. Referring to FIGS. 19A-D, needle 400 may be manufactured by providing a workpiece 480 that is fabricated of a malleable or deformable material, and machining the distal end 420 of workpiece 480 to create a trailing portion 440 and a leading portion 430, as illustrated in FIG. 19B. Any machining process known to one of skill in the art can be used to remove a portion of distal end 420 such as turning, drilling, milling, grinding, electrical discharge machining, electrochemical machining, abrasive flow machining, ultrasonic machining or other electrical, chemical or physical machining processes known to one of skill in the art. Preferably distal end 420 is ground or milled to create trailing portion 440 and leading portion 430. Referring to FIG. 19C, after trailing portion 440 and leading portion 430 are created in workpiece 480, leading portion 430 is pushed towards trailing portion 440. Referring to FIG. 19D, end 470 of leading portion 430 is then sharpened to a pointed tip 450 to form needle 400. End 470 can be sharpened by any means known in the art, such as by grinding or milling.

The present invention also contemplates delivery devices, such as syringes, or catheters, which have attached to the distal portions thereof, a needle according to any embodiment of the present invention to deliver infusion material to a target site. Such needles can then be used to deliver any type of infusion material, such as therapeutic agents, fluids such as saline and water, or diagnostic agents such as contrasting or radio-imaging agents to a target site. The target site can be, for example, an area of the body or any type of receptacle that is configured to receive the infusion material, such as a drug delivery port.

The areas of the body into which needles of the present invention can be inserted include any body lumina or organ such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, spinal column and the like. Although needles according to the present invention are not in any way limited to a specific application, they are particularly useful for reducing or preventing coring or other damage to tissue. For example, needles of the present invention are useful for inserting into the myocardial wall of the heart, which is accessed from a blood vessel or from the blood stream and that when accessed by needles known in the art, could result is a tissue core entering the blood stream. The needles of the present invention can also be used to deliver anesthesia, such as an epidural or spinal anesthesia, to the spinal column or to deliver any other drug intrathecally. Once again, because of the configuration of the needles of the present invention, excessive damage to the affected area of the spinal column may be minimized or eliminated.

Needles according to the present invention can also be used to collect a fluid sample from a fluid containment site of a body. In such an application, the needle is attached to the distal portion of a delivery device such as a syringe, and the needle is inserted into the fluid containment site of the body. A vacuum is created in the delivery device to collect the fluid sample from the fluid containment site. The fluid containment site can be any cavity, sac, or region in general of a body that stores or contains a fluid. Such fluids include, for example, blood, amniotic fluid, serous fluid, and cerebrospinal fluid. Accordingly, non-limiting examples of fluid containment sites include arteries and veins; the amniotic sac; serous cavities such as the peritoneal cavity, the pleural cavity, and the pericardial cavity; and the subarachnoid space.

A needle according to any embodiment of the present invention can also be used to access a drug delivery port, such as an intravascular drug access device (IVAD). Such drug delivery ports are used for the delivery of therapeutic agents and are typically implanted in a subcutaneous pocket, such as the anterior upper chest wall below the clavicle. As mentioned previously, the drug delivery ports usually include a chamber for the therapeutic agent and a pierceable septum for receipt of a needle to either fill or empty the chamber. The needles of the present invention can be used to introduce therapeutic agents into these drug delivery ports and because of the particular configuration of the needles of the present invention, damage to the septum is minimized even after repeated piercing of the septum. Of course, it will be understood to one of skill in the art that the needle can also be used to remove a therapeutic agent from the drug delivery port or to flush the drug delivery port with a saline solution, for example.

It should be emphasized that the above mentioned methods of using needles of the present invention are merely illustrative and such needles can be used for any other appropriate purpose or application.

The foregoing description has been set forth merely to illustrate the invention and is not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

I claim:

1. A needle comprising:
   a shaft having a heel, an open pointed tip, a longitudinal axis, and an infusion lumen extending through the shaft and the open tip; and
   a buffer within the infusion lumen, the buffer extending longitudinally along and in contact with an inner surface of the shaft, the buffer being offset from the longitudinal axis of the shaft such that a longitudinal axis of the buffer is not coincident with the longitudinal axis of the shaft, the buffer having a blunt distal end, and wherein in a fully extended position, the distal end abuts and occludes the heel of the shaft during insertion and cannot extend past the pointed tip.

2. The needle of claim 1, wherein in the fully extended position, the blunt distal end protrudes out of the infusion lumen of the shaft.

3. The needle of claim 1, wherein the blunt distal end is rounded.

4. The needle of claim 1, wherein the buffer is an elongated rod that spans the length of the infusion lumen.

5. The needle of claim 1, wherein the buffer has a cross-sectional area that is substantially less than a cross-sectional area of the infusion lumen.

6. The needle of claim 5, wherein the cross-sectional area of the buffer is approximately less than or equal to half that of the cross-sectional area of the infusion lumen.

7. The needle of claim 1, wherein the buffer has no lumen therein.

8. The needle of claim 1, wherein the buffer is fixedly attached to the inner surface of the shaft.

* * * * *